(12) United States Patent
Fantuzzi et al.

(10) Patent No.: US 7,713,523 B2
(45) Date of Patent: *May 11, 2010

(54) SOLUBILIZED COQ-10 AND CARNITINE

(75) Inventors: Michael Fantuzzi, Glendale, CA (US); Ronald G. Udell, Beverly Hills, CA (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 24 days.

This patent is subject to a terminal disclaimer.

(21) Appl. No.: 11/860,232

(22) Filed: Sep. 24, 2007

(65) Prior Publication Data

US 2008/0152707 A1    Jun. 26, 2008

Related U.S. Application Data

(63) Continuation of application No. 11/206,718, filed on Aug. 18, 2005, now Pat. No. 7,273,606, which is a continuation of application No. 10/792,648, filed on Mar. 3, 2004, now Pat. No. 7,169,385, which is a continuation-in-part of application No. 10/674,268, filed on Sep. 29, 2003.

(51) Int. Cl.
  *A61K 38/43*   (2006.01)
  *A61K 9/66*   (2006.01)
  *A61K 9/64*   (2006.01)
  *A61K 31/195*   (2006.01)
  *A61K 31/14*   (2006.01)

(52) U.S. Cl. ...................... 424/94.1; 424/455; 424/456; 514/642; 514/667

(58) Field of Classification Search ................ 424/94.1, 424/455, 456; 514/642, 667
See application file for complete search history.

(56) References Cited

U.S. PATENT DOCUMENTS

| | | | |
|---|---|---|---|
| 4,565,700 A | 1/1986 | Suzuki | |
| 4,599,232 A | 7/1986 | Bertelli | |
| 4,824,669 A | 4/1989 | Folkers et al. | |
| 5,310,578 A | 5/1994 | Thurn-Muller et al. | |
| 5,378,461 A | 1/1995 | Neigut | |
| 5,500,416 A | 3/1996 | Miyazawa et al. | |
| 5,626,849 A | 5/1997 | Hastings et al. | |
| 5,637,316 A | 6/1997 | Ribier et al. | |
| 5,670,320 A | 9/1997 | Wallace et al. | |
| 5,686,491 A | 11/1997 | Sherwood | |
| 5,756,291 A | 5/1998 | Griffin et al. | |
| 5,843,476 A | 12/1998 | Ribier et al. | |
| 5,889,062 A | 3/1999 | Hoppe et al. | |
| 5,912,272 A | 6/1999 | Hoppe et al. | |
| 5,948,443 A | 9/1999 | Riley et al. | |
| 5,976,568 A | 11/1999 | Riley | |
| 5,977,162 A | 11/1999 | Seidman | |
| 6,020,383 A | 2/2000 | Stone et al. | |
| 6,033,678 A | 3/2000 | Lorenzen | |
| 6,048,846 A | 4/2000 | Cochran | |
| 6,048,886 A | 4/2000 | Neigut | |
| 6,054,136 A | 4/2000 | Farah et al. | |
| 6,063,432 A | 5/2000 | Maxwell et al. | |
| 6,069,167 A | 5/2000 | Sokol | |
| 6,080,788 A | 6/2000 | Sole et al. | |
| 6,203,818 B1 | 3/2001 | Vester | |
| 6,232,346 B1 | 5/2001 | Sole et al. | |
| 6,261,575 B1 | 7/2001 | Hoppe et al. | |
| 6,300,361 B1 | 10/2001 | Chopra | |
| 6,300,377 B1 | 10/2001 | Chopra | |
| 6,335,361 B1 | 1/2002 | Hamilton | |
| 6,342,526 B1 | 1/2002 | Vervuert et al. | |
| 6,426,362 B1 | 7/2002 | Miller et al. | |
| 6,428,779 B1 | 8/2002 | Sauermann et al. | |
| 6,441,050 B1 | 8/2002 | Chopra | |
| 6,455,589 B1 | 9/2002 | Ames et al. | |
| 6,469,024 B2 | 10/2002 | Tino et al. | |
| 6,472,378 B2 | 10/2002 | von Borstel | |
| 6,479,069 B1 | 11/2002 | Hamilton | |
| 6,503,506 B1 | 1/2003 | Germano | |
| 6,503,523 B2 | 1/2003 | Hoppe et al. | |
| 6,506,915 B1 | 1/2003 | West | |
| 6,528,042 B1 | 3/2003 | Brown et al. | |
| 6,545,184 B1 | 4/2003 | Lipshutz | |

(Continued)

FOREIGN PATENT DOCUMENTS

DE   3512054   10/1986

(Continued)

OTHER PUBLICATIONS

R. Chopra et al., "A New Coenzyme Q10 Preparation with Enhanced Bioavailability", FASEB Journal, 11 3), pp. A586, 1997, Abstract.

(Continued)

*Primary Examiner*—Karen Cochrane Carlson
*Assistant Examiner*—Rosanne Kosson
(74) *Attorney, Agent, or Firm*—Dorsey & Whitney LLP

(57) ABSTRACT

The present invention is directed to compositions and methods of delivery of CoQ-10 and an amino acid solubilized in monoterpenes. Use of monoterpenes as dissolving agents, greatly effects the ability to incorporate greater amounts of bioactive CoQ-10 and the amino acid, such as carnitine, i.e., carnitine tartrate, in formulations, such as soft gel capsules.

21 Claims, No Drawings

U.S. PATENT DOCUMENTS

| | | | |
|---|---|---|---|
| 6,562,869 | B1 | 5/2003 | Hamilton et al. |
| 6,579,854 | B1 | 6/2003 | Mitchell et al. |
| 6,616,942 | B1 | 9/2003 | Udel |
| 7,169,385 | B2 | 1/2007 | Fantuzzi et al. |
| 7,273,606 | B2 | 9/2007 | Fantuzzi et al. |
| 7,588,786 | B2 | 9/2009 | Khan et al. |
| 2002/0098172 | A1 | 7/2002 | Udell et al. |
| 2003/0082168 | A1 | 5/2003 | Yegorova |
| 2003/0119781 | A1 | 6/2003 | Udell et al. |
| 2003/0147927 | A1 | 8/2003 | Khan et al. |
| 2003/0232076 | A1 | 12/2003 | Makino et al. |
| 2003/0232095 | A1 | 12/2003 | Garti et al. |
| 2004/0001874 | A1 | 1/2004 | Davidson et al. |
| 2004/0047922 | A1 | 3/2004 | Elstner |
| 2004/0126432 | A1 | 7/2004 | Hennen |
| 2004/0166157 | A1 | 8/2004 | Thombre |
| 2005/0025756 | A1 | 2/2005 | Erwin |
| 2005/0031681 | A1 | 2/2005 | Udell et al. |
| 2005/0036998 | A1 | 2/2005 | Udell |
| 2005/0037066 | A1 | 2/2005 | Udell et al. |
| 2005/0069582 | A1 | 3/2005 | Fantuzzi |
| 2005/0070611 | A1 | 3/2005 | Fantuzzi |
| 2005/0169983 | A1 | 8/2005 | Hassan et al. |
| 2006/0013888 | A1 | 1/2006 | Fantuzzi et al. |
| 2007/0269508 | A1 | 11/2007 | Udel |
| 2008/0003279 | A1 | 1/2008 | Udell |
| 2008/0020022 | A1 | 1/2008 | Udell |
| 2008/0089877 | A1 | 4/2008 | Udell et al. |
| 2008/0226710 | A1 | 9/2008 | Fantuzzi |

FOREIGN PATENT DOCUMENTS

| | | |
|---|---|---|
| EP | 0 882 450 | 1/1998 |
| EP | 0 888 774 | 1/1999 |
| JP | 55081813 | 6/1980 |
| JP | 57-042616 A1 | 3/1982 |
| JP | 59172417 | 9/1984 |
| WO | WO 98/40086 | 9/1998 |
| WO | WO 00/051574 | 9/2000 |
| WO | WO 02/09685 A1 | 2/2002 |
| WO | WO 03/105607 | 12/2003 |
| WO | WO 2004/066925 | 8/2004 |
| WO | WO 2005/032278 | 4/2005 |
| WO | WO 2005/092123 | 10/2005 |

OTHER PUBLICATIONS

M. Weis, et al., "Bioavailability of Four Oral Coenzyme Q10 Formulations in Healthy Volunteers", Molec. Aspects. Med., vol. 15, (Supplement) pp. s273-s280, 1994.

http://www.pformulate.com/pformsoftgel.htm.

CRC Handbook of Chemistry & Physics, $51^{st}$ Ed, R.C. Weast, Ed., The Chemical Rubber Co., Cleveland, 1970, pp. C-309, 356, 364, 392, 434, & 488.

Paul Karrer Biography, Nobel Prizes, Nobel Prize in Chemistry, http://nobelprize.org/nobel_prizes/chemistry/laureates/1937/karrer-bio.html, printed on Jan. 5, 2007.

T.R. Kommuru, et al. "Self-emulsifying drug delivery systems (SEDDS) of coenzyme Q10: formulation development and bioavailability assessment," International Journal of Pharmaceutics 212 (2001), pp. 233-246.

Oilseeds International Ltd., Rice bran oil- a health benefit, http://www.oilseedssf.com/products/prod_rice.html, 2002, printed on Mar. 6, 2006.

International Search Report dated Feb. 2, 2005, PCT/US2004/031775 [WO 05/032278], 3 pages.

International Search Report dated May 3, 2005, PCT/US2005/004781 [WO 05/092123], 3 pages.

RITO Partnership, Rice Bran Oil Info, http://web.archive.org/web/20020809203831/http://www.ricebranoil.info/why/index.html, web page of Aug. 9, 2002, printed from the Internet on Apr. 29, 2009.

Office Action (Restriction Requirement) dated Jan. 7, 2005, U.S. Appl. No. 10/674,268, 9 pages.

Response to Restriction Requirement dated Feb. 7, 2005, U.S. Appl. No. 10/674,268, 2 pages.

Office Action dated Mar. 11, 2005, U.S. Appl. No. 10/674,268, 8 pages.

Amendment and Response under 37 C.F.R. 1.111 dated Jun. 7, 2005, U.S. Appl. No. 10/674,268, 10 pages.

Office Action (Restriction Requirement) dated Jun. 28, 2005, U.S. Appl. No. 10/674,268, 7 pages.

Response to Restriction Requirement dated Jul. 27, 2005, U.S. Appl. No. 10/674,268, 10 pages.

Notice of Allowance and Fee(s) Due dated Aug. 26, 2005, U.S. Appl. No. 10/674,268, 11 pages.

Request for Continued Examination dated Sep. 15, 2005, U.S. Appl. No. 10/674,268, 1 page.

Declaration Under 37 C.F.R. 1.131 Antedating a Reference, dated Sep. 15, 2005, U.S. Appl. No. 10/674,268, 2 pages.

Office Action dated Sep. 30, 2005, U.S. Appl. No. 10/674,268, 8 pages.

Amendment and Response dated Dec. 20, 2005, U.S. Appl. No. 10/674,268, 13 pages.

Final Office Action dated Jan. 31, 2006, U.S. Appl. No. 10/674,268, 7 pages.

Response to Office Action Made Final, dated Apr. 28, 2006, U.S. Appl. No. 10/674,268, 14 pages.

Advisory Action dated May 22, 2006, U.S. Appl. No. 10/674,268, 4 pages.

Notice of Appeal dated May 31, 2006, U.S. Appl. No. 10/674,268, 2 pages.

Request for Continued Examination and Response to Office Action Made Final and Advisory Action dated Aug. 31, 2006, U.S. Appl. No. 10/674,268, 15 pages.

Final Office Action dated Sep. 15, 2006, U.S. Appl. No. 10/674,268, 8 pages.

Notice of Appeal dated Mar. 15, 2007, U.S. Appl. No. 10/674,268, 2 pages.

Request for Continued Examination and Response to Office Action Made Final dated Jul. 12, 2007, 16 pages.

Final Office Action dated Aug. 2, 2007, U.S. Appl. No. 10/674,268, 9 pages.

Response to Office Action Made Final, dated Oct. 8, 2007, U.S. Appl. No. 10/674,268, 12 pages.

Declaration Under Rule 1.131, dated Oct. 8, 2007, U.S. Appl. No. 10/674,268, 42 pages.

Advisory Action dated Oct. 25, 2007, U.S. Appl. No. 10/674,268, 14 pages.

Request for Continued Examination dated Oct. 30, 2007, U.S. Appl. No. 10/674,268, 2 pages.

Declaration Under Rule 1.131 dated Feb. 12, 2008, U.S. Appl. No. 10/674,268, 2 pages.

Advisory Action dated Mar. 3, 2008, U.S. Appl. No. 10/674,268, 3 pages.

Final Office Action dated Apr. 10, 2008, U.S. Appl. No. 10/674,268 6 pages.

Amendment and Response to Final Office Action dated Sep. 22, 2008, 17 pages.

Advisory Action dated Sep. 30, 2008, U.S. Appl. No. 10/674,268, 7 pages.

Notice of Appeal dated Oct. 10, 2008, U.S. Appl. No. 10/674,268, 2 pages.

Request for Continued Examination and Amendment and Response to Advisory Action of Sep. 30, 2008 and to Office Action of Apr. 10, 2008, dated Apr. 10, 2009, U.S. Appl. No. 10/674,268, 11 pages.

Office Action dated May 19, 2009, U.S. Appl. No. 10/674,268, 11 pages.

Restriction Requirement dated Oct. 31, 2005, U.S. Appl. No. 10/953,328, 5 pages.

Response to Restriction Requirement dated Nov. 29, 2005, U.S. Appl. No. 10/953,328, 8 pages.

Office Action dated Jan. 5, 2006, U.S. Appl. No. 10/953,328, 18 pages.

Amendment and Response dated Apr. 5, 2006, U.S. Appl. No. 10/953,328, 8 pages.
Office Action dated Apr. 26, 2006, U.S. Appl. No. 10/953,328, 9 pages.
Amendment and Response dated Oct. 26, 2006, U.S. Appl. No. 10/953,328, 14 pages.
Office Action (Restriction Requirement) dated Nov. 17, 2006, U.S. Appl. No. 10/953,328, 7 pages.
Response to Restriction Requirement dated Dec. 15, 2006, U.S. Appl. No. 10/953,328, 9 pages.
Final Office Action dated Jan. 18, 2007, U.S. Appl. No. 10/953,328, 13 pages.
Request for Continued Examination and Amendment and Response to Final Office Action dated Jul. 12, 2007, U.S. Appl. No. 10/953,328, 17 pages.
Final Office Action dated Aug. 7, 2007, U.S. Appl. No. 10/953,328, 11 pages.
Amendment and Response to Final Office Action dated Ocober 5, 2007, U.S. Appl. No. 10/953,328, 8 pages.
Declaration Under Rule 1.131 filed Oct. 5, 2007, U.S. Appl. No. 10/953,328, 38 pages.
Request for Continued Examination dated Oct. 29, 2007, U.S. Appl. No. 10/953,328, 2 pages.
Advisory Action dated Novnneber 1, 2007, U.S. Appl. No. 10/953,328, 4 pages.
Office Action dated Dec. 13, 2007, U.S. Appl. No. 10/953,328, 8 pages.
Declaration Under Rule 1.131 dated Feb. 12, 2008, U.S. Appl. No. 10/953,328, 2 pages.
Interview Summary dated Feb. 26, 2008, U.S. Appl. No. 10/953,328, 2 pages.
Amendment and Response to Office Action dated Apr. 14, 2008, U.S. Appl. No. 10/953,328, 28 pages.
Final Office Action dated Jun. 3, 2008, U.S. Appl. No. 10/953,328, 8 pages.
Amendment After Final (Under 37 C.F.R. 1.116) dated Nov. 3, 2008, U.S. Appl. No. 10/953,328, 19 pages.
Request for Continued Examination dated Nov. 25, 2008, U.S. Appl. No. 10/953,328, 2 pages.
Advisory Action dated Dec. 3, 2008, U.S. Appl. No. 10/953,328, 7 pages.
Final Office Action dated Jan. 21, 2009, U.S. Appl. No. 10/953,328, 9 pages.
Request for Continued Examination and Amendment and Response to Final Office Action dated May 21, 2009, U.S. Appl. No. 10/953,328, 19 pages.
Supplementary Declaration Pursuant to 37 C.F.R. 1.131 filed May 28, 2009, U.S. Appl. No. 10/953,328, 27 pages.
Interview Summary dated Jun. 1, 2009, U.S. Appl. No. 10/953,328, 3 pages.
Office Action (Restriction Requirement) dated Jun. 17, 2005, U.S. Appl. No. 10/792,648, 10 pages.
Response to Restriction Requirement dated Jun. 29, 2005, U.S. Appl. No. 10/792,648, 8 pages.
Notice of Allowance and Fee(s) Due and Interview Summary dated Jul. 29, 2005, U.S. Appl. No. 10/792,648, 12 pages.
Request for Continued Examination dated Sep. 14, 2005, U.S. Appl. No. 10/792,648, 2 pages.
Notice of Allowance and Fee(s) Due dated Sep. 30, 2005, U.S. Appl. No. 10/792,648, 5 pages.
Request for Continued Examination dated Oct. 14, 2005, U.S. Appl. No. 10/792,648, 2 pages.
Notice of Allowance and Fee(s) Due dated Feb. 15, 2006, U.S. Appl. No. 10/792,648, 5 pages.
Office Action dated Oct. 23, 2006, U.S. Appl. No. 11/206,718, 12 pages.
Amendment and Response dated Apr. 23, 2007, U.S. Appl. No. 11/206,718, 5 pages.
Terminal Disclaimer dated Apr. 23, 2007, U.S. Appl. No. 11/206,718, 2 pages.
Notice of Allowance and Fee(s) Due dated May 16, 2007, U.S. Appl. No. 11/206,718, 7 pagtes.

Office Action (Restriction Requirement) dated Dec. 7, 2005, U.S. Appl. No. 11/223,718, 5 pages.
Amendment and Response dated Jan. 6, 2006, U.S. Appl. No. 11/223,718, 5 pages.
Office Action dated Mar. 15, 2006, U.S. Appl. No. 11/223,718, 7 pages.
Amendment and Response dated Sep. 14, 2006, U.S. Appl. No. 11/223,718, 18 pages.
Final Office Action dated Oct. 2, 2006, U.S. Appl. No. 11/223,718, 8 pages.
Notice of Appeal dated Apr. 2, 2007, U.S. Appl. No. 11/223,718, 2 pages.
Request for Continued Examination and Response to Final Office Action dated Jun. 26, 2007, U.S. Appl. No. 11/223,718, 21 pages.
Final Office Action dated Jul. 20, 2007, U.S. Appl. No. 11/223,718, 10 pages.
Request for Continued Examination and Response to Final Office Action dated Oct. 2, 2007, U.S. Appl. No. 11/223,718, 10 pages.
Declaration Under Rule 1.131 filed Oct. 2, 2007, U.S. Appl. No. 11/223,718, 19 pages.
Office Action dated Oct. 30, 2007, U.S. Appl. No. 11/223,718, 9 pages.
Response to Office Action dated Nov. 30, 2007, U.S. Appl. No. 11/223,718, 19 pages.
Final Office Action dated Jan. 9, 2008, U.S. Appl. No. 11/223,718, 9 pages.
Declaration Under Rule 1.131 dated Feb. 12, 2008, U.S. Appl. No. 11/223,718, 2 pages.
Interview Summary dated Feb. 25, 2008, U.S. Appl. No. 11/223,718, 2 pages.
Amendment After Final Under 37 C.F.R. 1.116 dated Apr. 9, 2008, U.S. Appl. No. 11/223,718, 39 pages.
Advisory Action dated Apr. 23, 2008, U.S. Appl. No. 11/223,718, 5 pages.
Notice of Appeal dated Jun. 9, 2008, U.S. Appl. No. 11/223,718, 2 pages.
Request for Continued Examination and Amendment After Final Under 37 C.F.R. 1.114 dated Oct. 9, 2008, U.S. Appl. No. 11/223,718, 24 pages.
Final Office Action dated Nov. 17, 2008, U.S. Appl. No. 11/223,718, 11 pages.
Request for Cintinued Examination and Amendment and Response to Final Office Action dated May 18, 2009, U.S. Appl. No. 11/223,718, 19 pages.
Supplementary Declaration filed May 18, 2009, U.S. Appl. No. 11/223,718, 27 pages.
Notice of Non-Compliant Amendment dated May 21, 2009, U.S. Appl. No. 11/223,718, 2 pages.
Response to Notice of Non-Compliant Amendment dated JUn. 22, 2009, U.S. Appl. No. 11/223,718, 16 pages.
Padilla-Zakour, "Chemical Food Preservatives: Bonzoate and sorbate," *Venture*, New York State Agriculture Experimental Station, 1998, vol. 1, No. 2, 3 pages, found at URL: http://www.nysaes.cornell.edu/necfe/pubs/pdfNenture/venture2_chemical.html.
Bhandari, et al., "Preparation, Characterization and Evaluation of Coenzyme Q10 Binary Solid Dispersions for Enhanced Solubility and Dissolution," *Biol Pharm. Bull.*, 2007, vol. 30, No. 6, pp. 1171-1176.
Bliznakov, et al., "Biochemical and Clinical Consequencs of Inhibiting Coenzyme Q10 Biosynthesis by Lipid-Lowering HMG-COA Reductase Inhibitors (Statins): V Critical Overview," *Advances in Therapy*, Jul./Aug. 1998, vol. 15, No. 4, pp. 218-228.
Chopra, et al., "Relative Bioavailability of Coenzyme Q10 Formulations in Human Subjects," *Internat. J. Vit. Nutr. Res.*, 1988, vol. 68, pp. 109-113.
Density of Cooking Oil, *The Physics Factbook*, edited by Glenn Elert, dated unknown, 3 pages.
Dictionary.com accessed on Jan. 17, 2007, "thixotropic" 1 page.
Grant & Hackh's Chemical Dictionary, Definition of Gelatin, Fifth Edition, McGraw-Hill Book Company, 1987, p. 258.
Greenberg, et al., "Co-enzyme Q10: a new drug for cardiovascular disease," *The Journal of Clinical Pharmacology*, 1990, vol. 30, pp. 596-608.

Merriam-Webster Dictionary OnLine, definition of "elixir," http://www.merriam-webster.com/dictionary/elixir, printed from the Jun. 3, 2009, 2 pages.

Amendment and Response to Office Action dated Oct. 19, 2009, U.S. Appl. No. 10/674,268, 11 pages.

Office Action dated Jun. 22, 2009, U.S. Appl. No. 10/953,328, 9 pages.

Amendment and Response to Office Action dated Sep. 22, 2009, U.S. Appl. No. 10/953,328, 9 pages.

Final Office Action dated Oct. 23, 2009, U.S. Appl. No. 10/953,328, 9 pages.

Office Action dated Jul. 24, 2009, U.S. Appl. No. 11/223,718, 12 pages.

Amendment and Response to Office Action dated Oct. 26, 2009, U.S. Appl. No. 11/223,718, 9 pages.

Notice of Appeal dated Feb. 23, 2010, U.S. Appl. No. 10/953,328, 1 page.

Final Office Action dated Dec. 2, 2009, U.S. Appl. No. 11/223,718, 10 pages.

SOLUBILIZED COQ-10 AND CARNITINE

CROSS-REFERENCE TO RELATED APPLICATION(S)

This application is a continuation application and claims priority to U.S. patent application Ser. No. 11/206,718, filed Aug. 18, 2005, entitled "Solubilized CoQ-10 and Carnitine", which is a Continuation application of U.S. application Ser. No. 10/792,648, filed on Mar. 3, 2004, entitled Solubilized CoQ-10 and Carnitine", which claims priority to U.S. application Ser. No. 10/674,268, filed on Sep. 29, 2003, entitled "Solubilized CoQ-10", the contents of which are incorporated herein in their entirety by reference.

FIELD OF THE INVENTION

The present invention relates to the solubilization of coenzyme Q-10 and analogs thereof and/or carnitine and analogs thereof in at least one monoterpene, thereby providing increased bioavailability in delivery.

BACKGROUND OF THE INVENTION

CoQ-10 (coenzyme Q10) is a fat-soluble quinone that is structurally similar to vitamin K and commonly known as ubiquinone. CoQ-10 is found in most living organisms, and is essential for the production of cellular energy. CoQ-10 (2,3 dimethyl-5 methyl-6-decaprenyl benzoquinone) is an endogenous antioxidant found in small amounts in meats and seafood. Although CoQ-10 is found in all human cells, the highest concentrations of CoQ-10 occur in the heart, liver, kidneys, and pancreas. It is found naturally in the organs of many mammalian species.

CoQ-10 can be synthesized in the body or it can be derived from dietary sources. Situations may arise, however, when the need for CoQ-10 surpasses the body's ability to synthesize it. CoQ-10 can be absorbed by oral supplementation as evidenced by significant increases in serum CoQ-10 levels after supplementation.

CoQ-10 is an important nutrient because it lies within the membrane of a cell organelle called the mitochondria. Mitochondria are known as the "power house" of the cell because of their ability to produce cellular energy, or ATP, by shuttling protons derived from nutrient breakdown through the process of aerobic (oxygen) metabolism. CoQ-10 also has a secondary role as an antioxidant. CoQ-10, due to the involvement in ATP synthesis, affects the function of almost all cells in the body, making it essential for the health of all human tissues and organs. CoQ-10 particularly effects the cells that are the most metabolically active: heart, immune system, gingiva, and gastric mucosa Several clinical trials have shown CoQ-10 to be effective in supporting blood pressure and cholesterol levels. Furthermore, CoQ-10 has also been shown to improve cardiovascular health. CoQ-10 has been implicated as being an essential component in thwarting various diseases such as certain types of cancers. These facts lead many to believe that CoQ-10 supplementation is vital to an individual's well being.

CoQ-10 is sparingly soluble in most hydrophilic solvents such as water. Therefore, CoQ-10 is often administered in a powdered form, as in a tablet or as a suspension. However, delivery of CoQ-10 by these methods limits the bioavailability of the material to the individual.

Carnitine is a water-soluble vitamin like compound that the body utilizes to turn fat into energy. Carnitine works as part of an enzymatic complex formed from carnitine acyltransferase 1, carnitine translocase and carnitine transferase 11.

Carnitine is often used for heart conditions and it may be useful to treat angina or chest pain. Research has also shown that carnitine is also useful in the treatment of congestive heart failure and intermittent claudication. Although carnitine does not increase blood flow, it is believe that it helps muscles to better function under difficult painful circumstances, such as those associated with claudication.

The actions of carnitine and CoQ-10 are interrelated. In fact, carnitine, through beta-oxidation of fatty acids, is able to restore the energy supplies necessary for cell-life, whereas Coenzyme Q is able to restore the ATP supplies necessary for the energetic metabolic processes of the cell.

There is a need in the art for an improved methodology to deliver increased amounts of bioavailable CoQ-10 and/or an amino acid, such as carnitine to an individual in need thereof.

BRIEF SUMMARY OF THE INVENTION

The present invention pertains to the surprising discovery that ubiquinone (CoQ-10) and an amino acid such as carnitine can be readily dissolved in varying concentrations in a monoterpene. Generally, until the present discovery, most liquid delivery methods used for either CoQ-10 and/or an amino acid such as carnitine could solubilize only up to about 5% by weight of the CoQ-10 in the "solvent". Typical solvents included various oils or the combination of CoQ-10 and amino acid(s) was held in an aqueous suspension. The present invention provides the ability to solubilize both CoQ-10 and/or an amino acid such as carnitine in at least one monoterpene in concentrations of up to about 60% (weight to weight) without the need to aggressively heat the solution or with gentle warming. In particular, the solubilization of the CoQ-10 and/or amino acid with a monoterpene can be accomplished at ambient temperatures.

In one aspect, the present invention pertains to compositions that include coenzyme Q-10 or an analog thereof and/or an amino acid (or analog thereof, i.e., carnitine) with a sufficient quantity of a monoterpene that is suitable to solubilize said coenzyme Q-10, and/or an amino acid and, optionally, a pharmaceutically acceptable carrier. Generally, about 30 to about 45% of the CoQ-10 (by weight) is solubilized in the monoterpene and between about 0.5% to about 20% of the amino acid is solubilized (by weight) in the monoterpene. In particular, the range of the amino acid, such as a carnitine, is between about 0.2 to about 15%, more particularly, between about 0.5 and 10%, and even more particularly, between about 1.0% and about 2.0% (by weight of amino acid). In one particular aspect, the monoterpene is limonene. The compositions of the invention are useful as dietary supplements or as nutriceuticals.

In particular, the compositions of the invention are included in a soft gelatin (soft gel) capsule. Typically, the soft gelatin capsule includes at least 5% by weight of coenzyme Q-10 or an analog thereof and/or at least about 1.5 to about 2% by weight of an amino acid, i.e., carnitine or an analog thereof, solubilized in at least one monoterpene. Typical monoterpenes include, for example, perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

In another embodiment, the present invention pertains to methods for delivery of an effective amount of bioavailable CoQ-10; and/or an amino acid, such as carnitine, to an individual. The method includes providing CoQ-10 and/or an amino acid solubilized in a monoterpene, such that an effective amount of CoQ-10 and/or an amino acid is provided to the individual.

In still another embodiment, the present invention also includes packaged formulations of the invention that include at least one monoterpene as a solvent for CoQ-10 and/or an amino acid and instructions for use of the tablet, capsule, elixir, etc.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The present invention pertains to the surprising discovery that ubiquinone (CoQ-10) and/or an amino acid such as carnitine can be readily dissolved in varying concentrations in various monoterpenes. CoQ-10 is found in most living organisms, and is essential for the production of cellular energy. Ubiquinone is a naturally occurring hydrogen carrier in the respiratory chain (coenzyme Q) and structurally, it is a 2,3-dimethoxy-5-methyl-1,4-benzoquinone with a multiprenyl side chain, the number of isoprene units varying depending upon the organism from which it is derived. CoQ-10 analogs include reduced and semi-reduced CoQ-10 and ubiquinone derivatives described, for example, in WO 8803015, the teachings of which are incorporated herein by reference.

L-carnitine is recognized in the art and facilitates transport of materials through the mitochondrial membrane. L-carnitine is an essential fatty acid metabolism cofactor that helps to move fatty acids to the mitochondria from the cytoplasm. This is an important factor as this is where CoQ-10 uptake occurs.

In one aspect of the present invention, L-carnitine is included in soft gel formulations in combination with CoQ-10. Suitable ratios of L-carnitine and CoQ-10 are known in the art and include those described in U.S. Pat. No. 4,599,232, issued to Sigma Tau Industrie Faramaceutiche Riunite S.p.A. on Jul. 8, 1986, the teachings of which are incorporated herein in their entirety. In particular, combinations of limonene, CoQ-10 and L-carnitine in soft gel formulations are of importance. The present invention provides the advantage of solvating large amounts (relative to that of current state of the art) of CoQ-10 in limonene in a soft gel capsule along with an additive, such as L-carnitine.

It should be understood, that throughout the specification, reference is made to CoQ-10 or amino acids, such as carnitine, and that such reference includes the analogs thereof.

Generally, until the present discovery, most liquid delivery methods could solubilize only up at most about 10% by weight of the CoQ-10 and/or an amino acid in the "solvent. Typical solvents included oils or, for example, the CoQ-10 was held in an aqueous suspension. Alternatively, the CoQ-10 and/or the amino acid were provided as a solid in a tablet or powder.

The present invention provides the ability to solubilize CoQ-10 and/or amino acids in a monoterpene, as defined herein, in concentrations of up to about 60% (weight to weight) without the need to heat the solution. In one aspect, the monoterpene solubilizes CoQ-10 from about 0.1 percent by weight to about 45 percent by weight.

In particular, the solubilization of the CoQ-10 with monoterpenes can be accomplished at ambient temperatures. In one aspect, from about 5 to about 50 percent (weight CoQ-10/weight solvent) CoQ-10 can be solubilized in a monoterpene. In another aspect, from about 15 to about 40 percent w/w can be solubilized and in still another aspect, from about 20 to about 35 percent w/w CoQ-10 can be solubilized in a monoterpene.

In another aspect, the solubilization of an amino acid or an amino acid analog, such as carnitine, with one or more monoterpenes can be accomplished at ambient temperatures. In one aspect, from about 0.05 to about 0.5 percent (weight amino acid/weight solvent) amino acid can be solubilized in a monoterpene. In another aspect, from about 0.01 to about 0.25 percent w/w can be solubilized and in still another aspect, from about 0.02 to about 0.2 percent w/w amino acid can be solubilized in a monoterpene.

The term "amino acid" as used herein includes, but is not limited to, glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, hydroxylysine, carnitine, and other naturally occurring amino acids and analogs thereof.

For example amino acid analogs, such as carnitine "analogs" include acetylated products, fumarate derivatives and the like, and acceptable ammonium and metal salts thereof.

The term "carnitine" is also known as 3-Carboxy-2-hydroxy-N,N,N-trimethyl-1-propanaminium hydroxide, inner salt; (3-carboxy-2-hydroxypropyl)trimethylammonium hydroxide, inner salt; gamma-amino-beta-hydroxybutyric acid trimethylbetaine; gamma-trimethyl-beta-hydroxybutyrobetaine; 3-hydroxy-4-(trimethyl-ammonio)butanoate. See The Merck Index (1989), p. 281 and references cited therein. Therefore, "carnitine" and "carnitine analogs" includes, but is not limited to racemic or essentially pure L-carnitine (carnitine), or a corresponding alkanoyl-carnitine such as e.g. acetyl-carnitine or propionyl-carnitine, or a suitable salt of such compounds such as e.g. L-carnitine tartrate, L-carnitine fumarate, L-carnitine-magnesium-citrate, acetyl-L-carnitine tartrate, acetyl-L-carnitine-magnesium-citrate, or any mixture of the afore mentioned compounds.

Carnitine and carnitine analogs also include those described in U.S. Pat. Nos. 5,362,753, 4,687,782, 5,030,458, 5,030,657, 4,343,816, 5,560,928, 5,504,072, 5,391,550 and 5,240,961, the teachings of which are incorporated herein by reference in their entirety.

The phrase "sufficient quantity of a monoterpene suitable to solubilize" is therefore intended to mean that that amount of a monoterpene that will dissolve a component under a given set of conditions, generally, those at ambient temperature. This determination should be understood by one skilled in the art and can be determined by methods known in the art, such as by solubility studies.

One of the particular advantages of utilizing monoterpenes in combination with CoQ-10 and/or an amino acid is that the ingredient is dissolved by the monoterpene. That is, many formulations currently in the marketplace have CoQ-10, for example, present as a suspension; a situation where not all the CoQ-10 is dissolved. This reduces efficacy and the bioavailability of the CoQ-10 and/or the amino acid (if present). The present invention eliminates this disadvantage by solubilizing the components in the monoterpene.

A particular advantage in using monoterpenes is that the CoQ-10 does not have to be heated to dissolve into solution. This is important so that the CoQ-10 does not degrade upon dissolution.

The term "monoterpene" as used herein, refers to a compound having a 10-carbon skeleton with non-linear branches. A monoterpene refers to a compound with two isoprene units connected in a head-to-end manner. The term "monoterpene" is also intended to include "monoterpenoid", which refers to a monoterpene-like substance and may be used loosely herein to refer collectively to monoterpenoid derivatives as well as monoterpenoid analogs. Monoterpenoids can therefore include monoterpenes, alcohols, ketones, aldehydes, ethers, acids, hydrocarbons without an oxygen functional group, and so forth.

It is common practice to refer to certain phenolic compounds, such as eugenol, thymol and carvacrol, as monoterpenoids because their function is essentially the same as a monoterpenoid. However, these compounds are not technically "monoterpenoids" (or "monoterpenes") because they are not synthesized by the same isoprene biosynthesis pathway, but rather by production of phenols from tyrosine. However, common practice will be followed herein.

Suitable examples of monoterpenes include, but are not limited to, limonene, pinene, cintronellol, terpinene, nerol, menthane, carveol, S-linalool, safrol, cinnamic acid, apiol, geraniol, thymol, citral, carvone, camphor, etc. and derivatives thereof. For information about the structure and synthesis of terpenes, including terpenes of the invention, see Kirk-Othmer Encyclopedia of Chemical Technology, Mark, et al., eds., 22:709-762 3d Ed (1983), the teachings of which are incorporated herein in their entirety.

In particular, suitable limonene derivatives include perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

Formulation of the CoQ-10 and/or an amino acid can be accomplished by many methods known in the art. For example, the solubilized CoQ-10 can be formulated in a suspension, an emulsion, an elixir, a solution, a caplet that harbors the liquid, or in a soft gelatin capsule. Often the formulation will include an acceptable carrier, such as an oil, or other suspending agent.

Suitable carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carriers, beeswax can be used as a suitable carrier, as well as suspending agents such as silica (silicon dioxide).

The formulations of the invention are considered dietary supplements useful to the increase the amounts of CoQ-10 and/or amino acid(s) in individuals in need thereof.

Alternatively, the formulations of the invention are also considered to be nutraceuticals. The term "nutraceutical" is recognized in the art and is intended to describe specific chemical compounds found in foods that may prevent disease. CoQ-10 and amino acids are such compounds.

The formulations of the invention can further include various ingredients to help stabilize, or help promote the bioavailability of the CoQ-10 and/or amino acid(s), or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Vitamin(s), if present, are present in the composition of the invention in an amount ranging from about 5 mg to about 500 mg. More particularly, the vitamin(s) is present in an amount ranging from about 10 mg to about 400 mg. Even more specifically, the vitamin(s) is present from about 250 mg to about 400 mg. Most specifically, the vitamin(s) is present in an amount ranging from about 10 mg to about 50 mg. For example, B vitamins are in usually incorporated in the range of about 1 milligram to about 10 milligrams, i.e., from about 3 micrograms to about 50 micrograms of B12. Folic acid, for example, is generally incorporated in a range of about 50 to about 400 micrograms, biotin is generally incorporated in a range of about 25 to about 700 micrograms and cyanocobalamin is incorporated in a range of about 3 micrograms to about 50 micrograms.

Mineral(s), if present, are present in the composition of the invention in an amount ranging from about 25 mg to about 1000 mg. More particularly, the mineral(s) are present in the composition ranging from about 25 mg to about 500 mg. Even more particularly, the mineral(s) are present in the composition in an amount ranging from about 100 mg to about 600 mg.

Various additives can be incorporated into the present compositions. Optional additives of the present composition include, without limitation, phospholipids, L-carnitine, starches, sugars, fats, antioxidants, amino acids, proteins, flavorings, coloring agents, hydrolyzed starch(es) and derivatives thereof or combinations thereof.

As used herein, the term "phospholipid" is recognized in the art, and refers to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as camosol, camosic acid and rosmanol found in rosemary and hawthorn extract, proanthocyanidins such as those found in grapeseed or pine bark extract, and green tea extract.

The term "flavonoid" as used herein is recognized in the art and is intended to include those plant pigments found in many foods that are thought to help protect the body from cancer.

These include, for example, epi-gallo catechin gallate (EGCG), epi-gallo catechin (EGC) and epi-catechin (EC).

Any dosage form, and combinations thereof, are contemplated by the present invention. Examples of such dosage forms include, without limitation, chewable tablets, elixirs, liquids, solutions, suspensions, emulsions, capsules, soft gelatin capsules, hard gelatin capsules, caplets, lozenges, chewable lozenges, suppositories, creams, topicals, ingestibles, injectables, infusions, health bars, confections, animal feeds, cereals, cereal coatings, and combinations thereof. The preparation of the above dosage forms are well known to persons of ordinary skill in the art.

For example, health bars can be prepared, without limitation, by mixing the formulation plus excipients (e.g., binders, fillers, flavors, colors, etc.) to a plastic mass consistency. The mass is then either extended or molded to form "candy bar" shapes that are then dried or allowed to solidify to form the final product.

Soft gel or soft gelatin capsules can be prepared, for example, without limitation, by dispersing the formulation in an appropriate vehicle (e.g. rice bran oil, monoterpene and/or beeswax) to form a high viscosity mixture. This mixture is then encapsulated with a gelatin based film using technology and machinery known to those in the soft gel industry. The industrial units so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally limonene, in combination with rice bran oil and/or beeswax if desired) and can include, apart form the antioxidant actives, a hydrophilic matrix. The hydrophilic matrix, if present, is a polyethylene glycol having an average molecular weight of from about 200 to 1000. Further ingredients are optionally thickening agents. In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes are mature technologies and are all widely available to any one wishing to prepare soft gelatin capsules.

Typically, when a soft gel capsule is prepared, the total weight is between about 250 milligrams and about 2.5 gram in weight, e.g., 400-750 milligrams. Therefore, the total weight of additives, such as vitamins and antioxidants, is between about 80 milligrams and about 2000 milligrams, alternatively, between about 100 milligrams and about 1500 milligrams, and in particular between about 120 milligrams and about 1200 milligrams. In particular, the soft gel capsule typically weighs between about 1000 milligrams and 1300 milligrams, wherein the percentage fill is about 50% of the entire weight of the capsule, i.e., from about 500 to about 650 milligrams fill weight. The fill weight includes the active ingredient(s), solubilizing agents, etc.

Preparation of the soft gel capsules was accomplished by methods well known in the art including, but not limited to those described throughout the specification and in U.S. Pat. Nos. 6,616,942, 6,623,734 and pending U.S. Ser. Nos. 10/035,753 and 09/825,920, the contents of which are incorporated herein by reference in their entirety.

For example, a soft gel capsule can be prepared by mixing a 35% solution of CoQ-10 (by weight) and a 26% solution of an amino acid, such as carnitine (by weight), and limonene (w/w/w) (e.g., 104 milligrams of CoQ-10, 228 milligrams carnitine tartrate in 470.5 milligrams of limonene) with between about 0.01 grams and about 0.4 grams (e.g., 0.1 grams) tocopherol, between about 200 grams and about 250 grams (e.g., 225 grams) rice bran oil and between about 0.01 grams and about 0.5 grams betacarotene (e.g. about 0.02 grams). The mixture is then combined with encapsulated within a gelatin capsule as described above.

The present invention also provides packaged formulations of a monoterpene with CoQ-10 and/or an amino acid such as carnitine and instructions for use of the tablet, capsule, elixir, etc. Typically, the packaged formulation, in whatever form, is administered to an individual in need thereof that requires an increase in the amount of CoQ-10 and/or the amino acid in the individual's diet. Typically, the dosage requirement is between about 1 to about 4 dosages a day.

CoQ-10 has been implicated in various biochemical pathways and is suitable for the treatment of cardiovascular conditions, such as those associated with, for example, statin drugs that effect the body's ability to product CoQ-10 naturally. CoQ-10 has also been implicated in various periodontal diseases. Furthermore, CoQ-10 has been implicated in mitochondrial related diseases and disorders, such as the inability to product acetyl coenzyme A, neurological disorders, for example, such as Parkinson's disease and, Prater-Willey syndrome.

The following examples are intended to be illustrative only and should not be considered limiting.

EXAMPLES

Formulations of CoQ-10 and an amino acid, such as carnitine, can be prepared in the following ratios by mixing the components together and then placing into a soft gel capsule.

| Component | Example 1 | Example 2 |
|---|---|---|
| CoQ-10 | 104.09 mg | 104.09 mg |
| Carnitine tartrate | 227.69 mg | 196.02 mg |
| Mixed Tocopherols (372 IU/g) | 269.03 mg | 269.03 mg |
| Rice Bran Oil | 176.02 mg | 0 |
| Natural Beta Carotene (20% by weight) | 10.05 mg | 10.05 mg |
| Yellow Beeswax | 20.0 mg | 0 |
| D-limonene | 0 mg | 227.69 mg |
| Total weight | 796 mg | 796 mg |

Example 2 demonstrates that the use of limonene solubilizes CoQ-10 and carnitine tartrate without the requirement of beeswax and/or rice bran oil being present. Examples 1 and 2 could be incorporated into soft gel capsules by standard methods known in the art and as described herein.

| Component | Example 3 | Example 4 |
|---|---|---|
| CoQ-10 | 104.08 mg | 104.08 mg |
| Carnitine (tartrate) | 4.50 mg | 78 mg |
| D-Limonene | 191.42 mg | 167.92 mg |
| 5-67 Tocopherol | 50 mg (50 IU) | 100 mg (100 IU) |

Examples 3 and 4 demonstrate that CoQ-10 and carnitine tartrate can be solubilized in scalable quantities. Additives, such as EPAX 2050 TG (an ω-3 oil; 20% EPA/50% DHA as triglycerides, remainder fatty acid/triglycerides; Pronova Biocare) and tocopherols (5-67 Tocopherol; BD Industries) can easily be incorporated into such limonene containing formulations. The resultant mixtures contained approximately 100 mg of CoQ-10 and ranges of carnitine (based on carnitine tartrate) per soft gel capsule. Preparation of the soft gel capsules was accomplished by methods well known in the art and as described herein.

Although the present invention has been described with reference to preferred embodiments, persons skilled in the art will recognize that changes may be made in form and detail without departing from the spirit and scope of the invention.

All literature and patent references cited throughout the application are incorporated by reference into the application for all purposes.

What is claimed is:

1. A composition, comprising: coenzyme Q-10, carnitine and a sufficient quantity of limonene to solubilize said coenzyme Q-10 and carnitine.

2. The composition of claim 1, wherein said coenzyme Q-10 is selected from the group consisting of coenzyme Q-10, reduced coenzyme Q-10 and semi-reduced coenzyme Q-10.

3. The composition of claim 1, wherein said coenzyme Q-10 is solubilized in said limonene in an amount between about 0.1% and about 45% by weight.

4. The composition of claim 1, wherein said coenzyme Q-10 is solubilized in said limonene in an amount between about 10% and about 40% by weight.

5. The composition of claim 1, wherein said composition further comprises rice bran oil.

6. The composition of claim 1, wherein said composition further comprises beeswax.

7. The composition of claim 1, wherein said composition further comprises an antioxidant.

8. A method of supplementing coenzyme Q-10 in a subject in need thereof, comprising the step of administering an effective amount of a composition comprising coenzyme Q-10, carnitine and a sufficient quantity of limonene to solubilize said coenzyme Q-10 and carnitine.

9. The method of claim 8, wherein said coenzyme Q-10 is selected from the group consisting of coenzyme Q-10, reduced coenzyme Q-10 and semi-reduced coenzyme Q-10.

10. The method of claim 8, wherein said coenzyme Q-10 is solubilized in said limonene in an amount between about 0.1% and about 45% by weight.

11. The method of claim 8, wherein said coenzyme Q-10 is solubilized in said limonene in an amount between about 10% and about 40% by weight.

12. The method of claim 8, wherein said composition further comprises rice bran oil.

13. The method of claim 8, wherein said composition further comprises beeswax.

14. The method of claim 8, wherein said composition further comprises an antioxidant.

15. A method of supplementing coenzyme Q-10 in a subject in need thereof, comprising the step of administering an effective amount of a composition of coenzyme Q-10 encapsulated in a soft gelatin capsule, comprising coenzyme Q-10, carnitine and a sufficient quantity of limonene to solubilize said coenzyme Q-10 and carnitine within said soft gelatin capsule.

16. The method of claim 15, wherein said coenzyme Q-10 is selected from the group consisting of coenzyme Q-10, reduced coenzyme Q-10 and semi-reduced coenzyme Q-10.

17. The method of claim 15, wherein said coenzyme Q-10 is solubilized in said limonene in an amount between about 0.1% and about 45% by weight.

18. The method of claim 15, wherein said coenzyme Q-10 is solubilized in said limonene in an amount between about 10% and about 40% by weight.

19. The method of claim 15, wherein said soft gelatin capsule further comprises rice bran oil.

20. The method of claim 15, wherein said soft gelatin capsule further comprises beeswax.

21. The method of claim 15, wherein said soft gelatin capsule further comprises an antioxidant.

* * * * *